United States Patent [19]

Parker et al.

[11] Patent Number: 5,750,906
[45] Date of Patent: May 12, 1998

[54] MULTIFUNCTION VALVE

[75] Inventors: Norman K. Parker, Northfield; James E. Rasmussen, Plainville; Richard L. Schulkind, Sharon; Kevin J. Sullivan, Medfield; Robert B. Green, Hopkinton, all of Mass.

[73] Assignee: Chiron Diagnostics Corporation, E. Walpole, Mass.

[21] Appl. No.: 739,249

[22] Filed: Oct. 29, 1996

Related U.S. Application Data

[60] Provisional application No. 60/006,741 Nov. 2, 1995.

[51] Int. Cl.$^6$ .................................................. G01N 1/10
[52] U.S. Cl. .................... 73/863.73; 73/864.86; 73/864.21; 422/63
[58] Field of Search ............... 73/863.72, 863.73, 73/864.84, 863.86, 863.84, 864.21, 864.24; 422/63, 100

[56] References Cited

U.S. PATENT DOCUMENTS

| | | | |
|---|---|---|---|
| 3,100,984 | 8/1963 | Martin | 73/863.73 |
| 4,289,029 | 9/1981 | Sampson et al. | 73/863.84 |
| 4,297,903 | 11/1981 | Buzza | 73/864.22 |
| 4,458,541 | 7/1984 | Deming et al. | 73/863.73 |
| 4,591,568 | 5/1986 | Banno et al. | 436/180 |
| 4,649,028 | 3/1987 | Kaltenbach et al. | 422/100 |
| 4,686,479 | 8/1987 | Young et al. | 324/439 |
| 4,749,658 | 6/1988 | Jaekel et al. | 436/180 |
| 4,764,342 | 8/1988 | Kelln et al. | 422/72 |
| 4,774,057 | 9/1988 | Uffenheimer et al. | 422/100 |
| 4,835,477 | 5/1989 | Polaschegg | 324/439 |
| 4,921,677 | 5/1990 | Hinckley et al. | 422/103 |
| 4,999,307 | 3/1991 | Oakley | 436/180 |
| 5,012,845 | 5/1991 | Averette | 73/864.84 |
| 5,055,263 | 10/1991 | Meltzer | 422/65 |
| 5,132,088 | 7/1992 | Wakatake | 122/63 |
| 5,183,765 | 2/1993 | Qureshi et al. | 436/180 |
| 5,213,766 | 5/1993 | Flesher et al. | 422/102 |
| 5,248,480 | 9/1993 | Greenfield et al. | 422/68 |
| 5,262,049 | 11/1993 | Ferkany | 210/258 |
| 5,270,211 | 12/1993 | Kelln et al. | 436/43 |
| 5,270,219 | 12/1993 | DeCastro et al. | 436/180 |
| 5,279,796 | 1/1994 | Parker et al. | 422/100 |
| 5,312,757 | 5/1994 | Matsuyama et al. | 436/54 |
| 5,360,423 | 11/1994 | McCormick | 604/403 |
| 5,366,904 | 11/1994 | Qureshi et al. | 436/180 |
| 5,372,782 | 12/1994 | Karkantis et al. | 422/63 |
| 5,380,486 | 1/1995 | Anami | 422/63 |
| 5,391,499 | 2/1995 | Karkantis et al. | 436/180 |
| 5,395,347 | 3/1995 | Blecher et al. | 604/198 |

*Primary Examiner*—Hezron E. Williams
*Assistant Examiner*—Nashmiya Ashraf
*Attorney, Agent, or Firm*—Arthur S. Morgenstern; Gordon R. Moriarty; Robert P. Blackburn

[57] ABSTRACT

The invention features a sample probe and reagent selector valve that enables selection among multiple functions of withdrawing a biological sample from a syringe or capillary into a fluid parameter sensor module, providing calibration and quality control reagents to the sensor module, and flowing a washing fluid through intake passages to prevent cross-contamination and clogging. The valve and sensor module are used in conjunction with an automated analytical instrument, such as an automated blood analyzer, to increase the speed of the analysis, minimize cross contamination between samples, and to overcome the inherent dangers of using the conventional needle/syringe or capillary methods of withdrawing fluids to be tested. The design of the valve provides performance benefits in the form of lower sample and reagent waste volumes, elimination of auxiliary valves and manifolds, and superior performance and reduced cost.

17 Claims, 7 Drawing Sheets

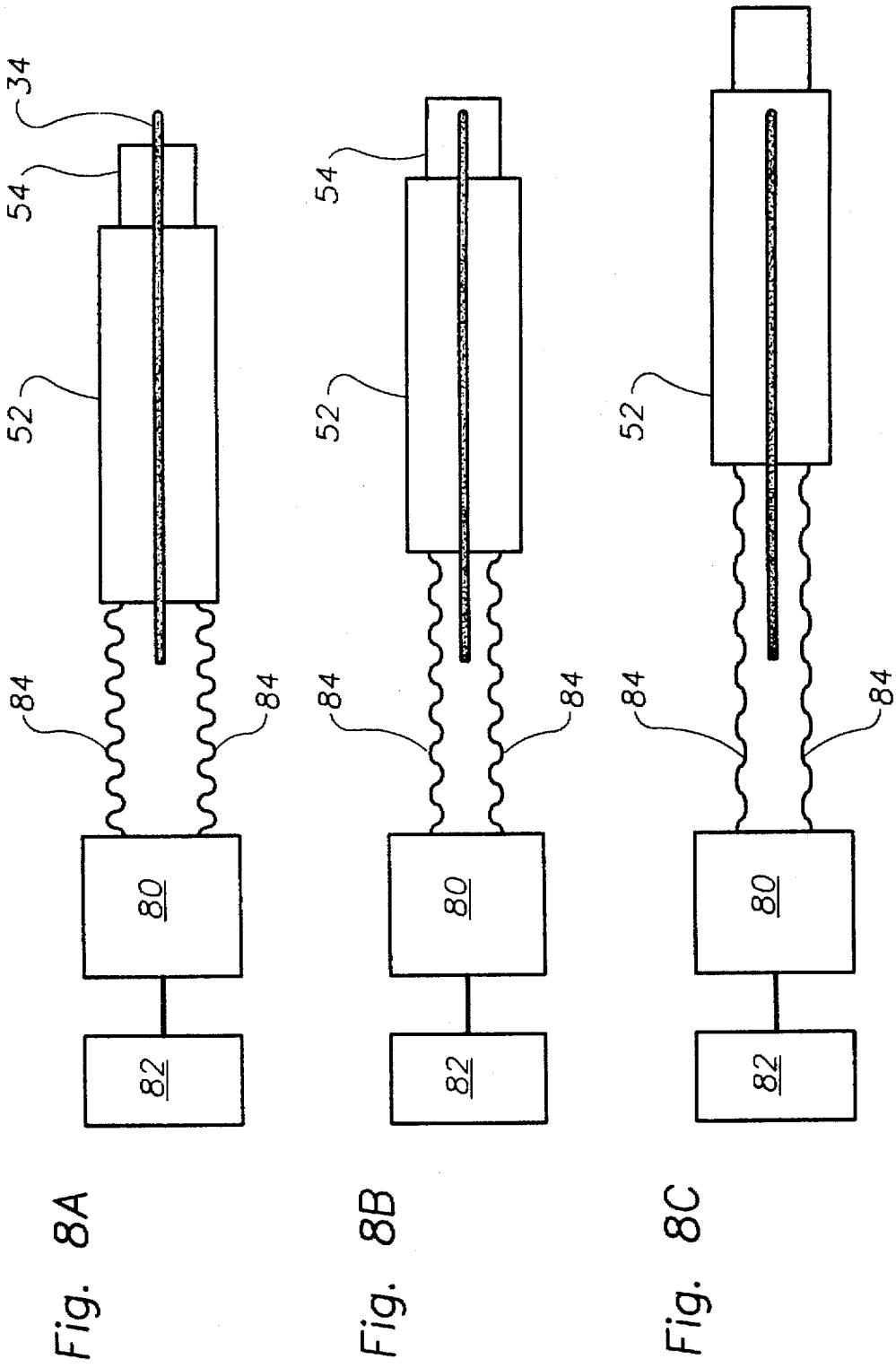

MULTIFUNCTION VALVE

This application claim the benefit of U.S. Provisional application Ser. No. 60/006,741 Nov. 2, 1995.

FIELD OF THE INVENTION

This invention relates to sample handling valves, and more particularly to combination reagent selection and sample probe valves for an automated instrument.

BACKGROUND OF THE INVENTION

A variety of methods are currently available to deliver a fluid sample to the analysis section of an instrument. In the case of liquid biological samples, syringes are often used to manually inject the sample into a sample receiving port on the instrument and into the analytical components of the instrument. Although simple, this method suffers from several disadvantages. In particular, the inconsistency of human control used to inject the sample causes variations between operators, between samples injected by the same operator, and throughout the injection motion of a single sample. These inconsistencies frequently result in different sample sizes being injected, and hence inconsistent analytical results. Proper injection technique using a syringe thus requires proper training and adequate time to master.

Another significant problem with manual syringe injection is contamination of the sample. When a syringe is used, the needle is generally pushed through a septum or other seal prior to injection into the instrument. If the septum is contaminated with materials from previous injections, the composition of the sample that is currently being analyzed could be tainted and result in cross-contamination between samples. Under heavy use, septa are also liable to becoming clogged with residual material from previous samples. One method to alleviate sample contamination is to manually wash the syringe and injector, and recalibrate the instrument. However, this method is tedious and time-consuming and itself not always consistent.

Laboratory safety has become a significant consideration recently, particularly with the threat of blood-borne diseases, such as hepatitis and AIDS. Use of a conventional syringe and needle increases the risk of exposing the laboratory technicians to infected blood through accidental skin puncture. In addition, careless disposal of the contaminated syringe and/or needle can result in exposure of other laboratory and maintenance personnel to blood-borne diseases.

Uptake of a sample by a capillary is an alternative method over manual syringe injection. However, special robotic-type equipment must often be attached to the instrument in order for a sample to be drawn into the capillary and transported to the analyzer. Capillaries also require manual cleaning between samples, and must be replaced at regular intervals to maintain performance consistency and sample quality. Ideally, an injection and sampling system should reproducibly and repeatedly inject samples into an analyzer instrument with minimal cross contamination between samples. The injection and sampling system should also be able to recalibrate the instrument automatically and be able to choose from a variety of standardization reagents to match the composition of a variety of samples.

U.S. Pat. Nos. 5,372,782 and 5,391,499 to Karkantis et al. disclose automated sampling devices. However, these devices are limited in the number of standardization reagents that may be chosen.

SUMMARY OF THE INVENTION

The invention features a sample probe and reagent selector valve that performs the multiple functions of withdrawing a liquid biological sample from a syringe or capillary, providing calibration and quality control reagents to the sensor module, and washing itself to prevent cross-contamination and clogging. The valve is used in conjunction with an automated analytical instrument, such as an automated blood analyzer, to increase the speed of the analysis, minimize cross contamination between samples, and to overcome the inherent dangers of using the conventional needle/syringe or capillary methods of injection. The design of the valve provides performance benefits in the form of lower sample and reagent waste volumes, elimination of auxiliary valves and manifolds, and superior performance and reduced cost.

The invention thus features a sample probe and selector valve that includes a lower valve body, an upper valve body, and a sample probe movably positioned between the upper and lower valve bodies. The sample probe is positioned in a channel molded into the upper and lower valve bodies when the upper and lower valve bodies are assembled together. The sample probe moves linearly within the channel to permit the selective uptake of either a sample, a wash solution or foam, or quality control or calibration reagents.

The lower valve body includes two or more inlet ports that permit calibration or quality control reagents to flow into the analytical section of the device. The sample probe takes the form of a tube sealed at one end and includes two apertures located on the walls of the tube, similar to the arrangement found in a basketball filling needle. One aperture is located adjacent to the sealed end of the sample probe, and the second aperture is located between the first aperture and the opposite open end. The distance between the two probe apertures is such that when the second aperture aligns with any one of the inlet ports on the lower valve body, the first aperture is sealed by the two halves of the valve. Similarly, when the first aperture is positioned beyond the first end of the valve, the second aperture becomes sealed between the two halves of the valve. Thus, as the valve body and sample probe move relative to each other, the apertures on the sample probe are either sealed or in the appropriate positions for uptake of a sample, washing of the sample probe, or uptake of calibration or quality control reagents.

The invention also features a combination sample input collector and wash chamber attached to the front of the multifunction valve. The sample input collector includes a fitting designed to accept a container containing a sample to be analyzed; for example a syringe or capillary containing a sample of blood, urine, or other biological sample. A washing solution or foam is provided by a pump to a wash port and channel formed in the lower valve body and connected to the wash chamber.

Thus, the multifunction valve of the invention also features a position in which the tip and interior of the sample probe may be washed between samples. According to the invention, when the tip of the sample probe is positioned within the wash chamber, washing solution or foam is pumped into the wash chamber and flows around the outside of the sample probe. Simultaneously, the wash solution can be aspirated into the sample probe to clean the interior of the sample probe and analyzer between analyses.

The multifunction valve of the invention also features a position in which reagents, such as calibration, quality control, or other reagents, may be transported into the analysis section of the instrument. According to the invention, when the second aperture of the sample probe is aligned with a selected one of the inlet ports, a quality control or calibration reagent may be aspirated into the analytical section of the instrument to affect calibration and/or quality control of the instrument between samples. In this position, the first aperture is sealed between the upper and lower valve bodies to prevent the calibration or quality control reagents from escaping the valve. An additional position is present which allows for quality control reagents to be aspirated using the first aperture while the second aperture is sealed. This position allows for automatic aspiration of quality control reagent in a manner consistent with the aspiration of samples.

The invention also encompasses an analytical instrument that uses the multifunction valve described above. In the analytical instrument, the multifunction valve is attached to pumps, reagent containers, and motion and control apparatus to move the multifunction valve. The pumps include a first pump to aspirate the sample into the analytical instrument and a second pump to provide wash solution to the combination sample input collector and wash chamber. Reagent containers are connected to the input ports on the lower valve body to provide calibration or quality control solutions to the instrument. Thus, the multifunction valve of the invention functions as a major control point in the automated analysis of biological material.

DESCRIPTION OF THE DRAWINGS

The invention will be more fully understood from the following detailed description taken in conjunction with the accompanying drawings in which:

FIG. 8A is a diagram of the motion and control apparatus associated with the multifunction valve of the invention in the "sampling" position;.

FIG. 8B is a diagram of the motion and control apparatus associated with the multifunction valve of the invention in the "wash" position; and FIG. 8C is a diagram of the motion and control apparatus associated with the multifunction valve of the invention in the "reagent uptake" position.

DETAILED DESCRIPTION OF THE INVENTION

Figure 1:
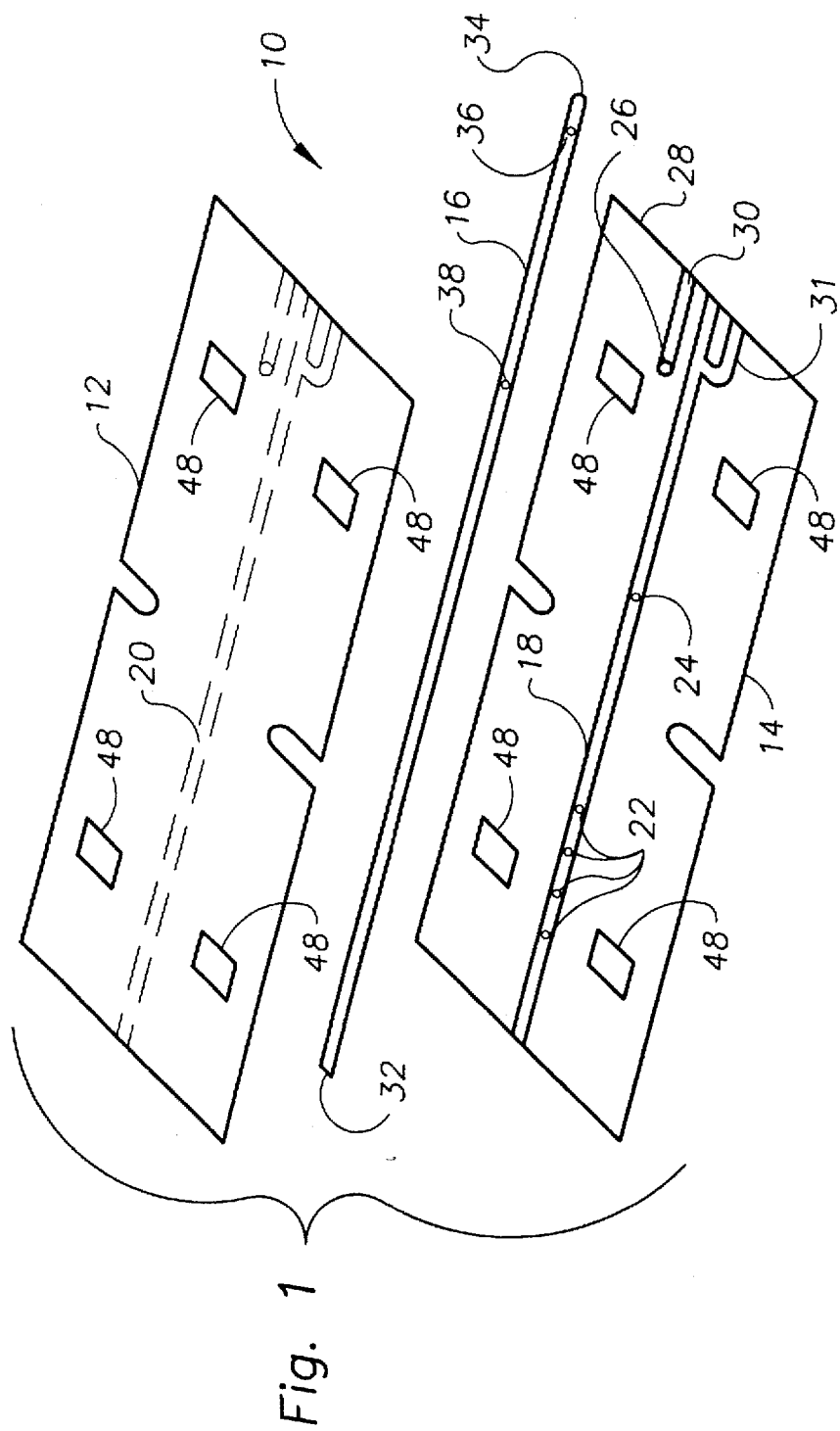
FIG. 1 is an exploded view of the multifunction valve of the invention.

FIG. 1 shows an exploded overview of the multifunction valve 10 of the invention. The multifunction valve 10 comprises an upper valve body 12, a lower valve body 14, and a sample probe 16. The lower valve body includes a lower groove 18 formed along its longitudinal axis, and the upper valve body includes an upper groove 20 formed along its longitudinal axis. The upper valve body 12 and the lower valve body 14 are fit together and the respective grooves 18 and 20 in each valve body form a channel in which the sample probe 16 is positioned. The sample probe 16 is capable of sliding within the channel and thus permits the multifunction valve to operate. The halves of the multifunction valve are held together by snap action clamps or other attachment devices. Recesses 48 are used to accurately align the upper valve body 12 and the lower valve body 14 when assembled together.

As illustrated in FIG. 1, the lower valve body 14 includes a plurality of inlet ports 22 formed in the groove 18. The inlet ports 22 permit the multifunction valve to be coupled to a variety of solutions, such as quality control or calibration reagents that are utilized during the analysis cycle. A vent aperture 24 is positioned along the groove 18 and ahead of the inlet ports 22 to allow the valve to vent to the atmosphere or allow quality control or standardization reagents to be automatically aspirated into the instrument. The vent aperture permits uptake of air between samples and provides a method of cleaning the interior of the sample probe by meniscus surface tension. A wash port 26 is positioned near the front end 28 of the lower valve body. A channel 30 permits wash fluid to flow from the wash port 26 to the front end 28 of the valve body. An elbow channel 31 is formed in the lower valve body 12 between the groove 18 and the front end 28. The elbow channel 31 allows for a drain port at the bottom of the sample input collector and wash chamber 54 to eliminate residual fluid, improve washing and permit venting of the system.

Referring again to FIG. 1, the sample probe 16 fits into the channel formed by the respective grooves 18 and 20 when the two halves of the multifunction valve are assembled. The sample probe 16 is an elongated tube and includes an open end 32 and a sealed end 34. The sample probe 16 is capable of sliding in the channel to affect the multiple functions of the valve, such as sample uptake, wash, or reagent uptake.

In the sample probe, a sample aperture 36 is located on the wall of the probe adjacent to the sealed end 34 in an arrangement similar to that found on the needle valves that fill footballs, basketballs and the like. A reagent aperture 38 is located on the wall of the sample probe between the sample aperture 36 and the open end 32. The relative distance between the sample aperture 36 and the reagent aperture 38 is such that when the reagent aperture 38 aligns with any one of the inlet ports 22 on the lower valve body, the sample aperture 36 is sealed by the two halves of the valve, and when the sample aperture 36 is positioned beyond the front end 28 of the valve, the reagent aperture 38 becomes sealed between the two halves of the valve. Similarly, when the sample aperture 36 is aligned with the vent aperture, the reagent aperture 38 is sealed between the two valve bodies. Thus, as the assembled valve bodies move relative to the sample probe 16, the apertures 36, 38 are either sealed or in the appropriate positions for uptake of a sample, washing of the sample probe, or uptake of calibration or quality control reagents. In one embodiment, the probe is stationary and the valve body (and sample) are moveable. Alternatively, the sample probe can be moved and the valve body held stationary.

Figure 2A:
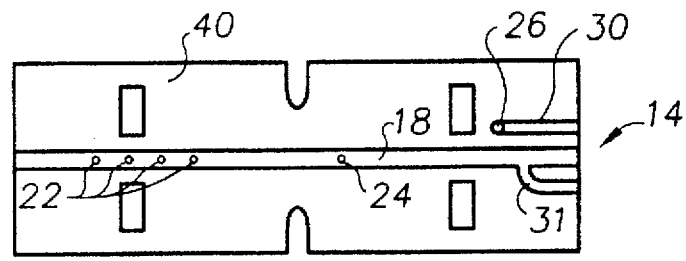
FIG. 2A is a top view of the lower valve body of the invention.

FIG. 2A shows the upper face 40 of the lower valve body 14 in more detail. The lower valve body 14 can be made of any flexible material, such as rubber, neoprene, or similar polymer known in the art, that is capable of forming a seal between itself and the interconnections and sample probe described herein below. The upper face 40 of the lower valve body 14 includes a groove 18 running longitudinally along its entire length.

Located in the groove are a plurality of inlet ports 22 that permit a plurality of reagents to flow into the interior of the valve body. The reagents may be quality control reagents, calibration reagents, or other chemical reagents known in the art. It is also possible to conduct chemical reactions in the sample probe if the appropriate reagents are supplied throughout the inlet ports 22. The plurality of inlet ports permits the chosen reagents to be selected and dispensed at the appropriate time in the analytical procedure. The inlet ports have a diameter less than the inner diameter of the sample probe and preferably in the range of 20–80% of the sample probe diameter.

Figure 2B:
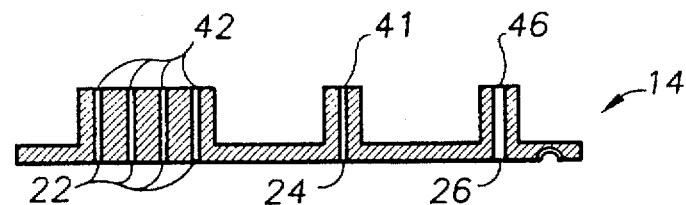
FIG. 2B is a side view of the lower valve body of the invention.
Figure 2C:
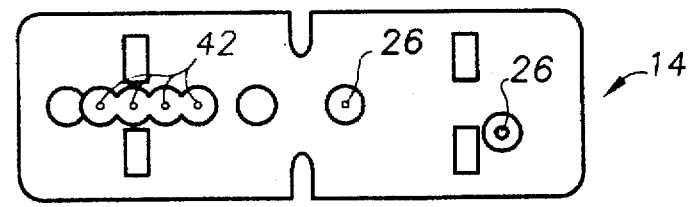
FIG. 2C is a bottom view of the lower valve body of the invention.

As shown in FIG. 2B, the inlet ports 22 are accessible to the groove 18 by a plurality of inlet tubes 42 formed in the valve body 14 with one tube being associated with each port. The inlet tubes allow reagents to flow into the sample probe 16 if the reagent aperture 38 is aligned with one of the inlet ports. While the reagent aperture 38 is aligned with a selected inlet port, the sample aperture 36 is sealed by the flexible material of the valve bodies as described in more detail below. As shown in FIGS. 2B and 2C, the vent aperture 24 is also connected to the groove 18 by a vent inlet tube 44. The vent inlet tube 44 may be connected to a source of gas, such as pressurized air, nitrogen, argon, etc. to provide a gas source to the sample probe. Inlet tube 44 may also be connected to a reagent delivery system capable of delivery quality control reagents such that the system can perform automatic quality control procedures. Alternatively, the vent aperture may be vented to the atmosphere to provide a space between consecutive samples. Wash port 26 is connected to the groove 18 by a wash inlet tube 46, and permits the wash port to be connected to a pump that will provide wash solution or foam when the sample probe is to be washed.

It will be appreciated that while the embodiment shown in FIG. 2 illustrates the invention with four reagent inlet ports 22, other numbers of reagent inlet ports, such as 2, 3, 5, 6, 10, or more may be formed in the lower valve body 14, and that the number of reagent inlet ports may be determined empirically by one skilled in the art.

Figure 3:
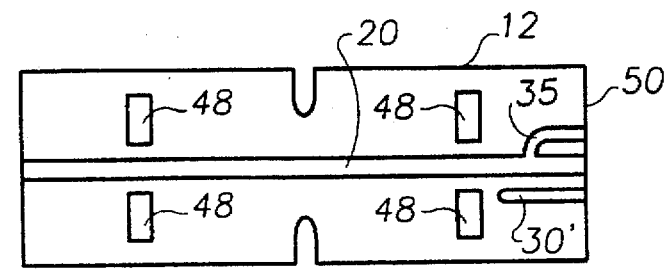
FIG. 3 is a bottom view of the upper valve body of the invention.
Figure 3A:
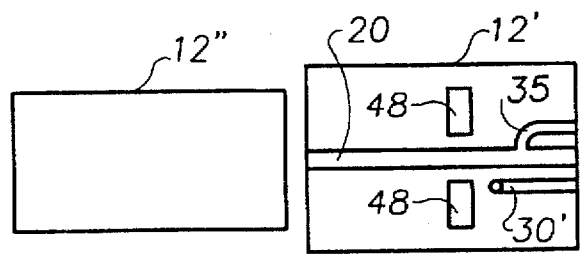
FIG. 3A is a bottom view of an alternative embodiment of the upper valve body of the invention.

FIG. 3 illustrates a bottom view of the upper valve body 12. The upper valve body 12 includes a groove 20 that runs longitudinally along its entire length to guide the probe during operation. A wash channel 30' is formed to run parallel to the groove 20 and terminate at the front end 50 of the upper valve body 12. Similarly, a complementary elbow channel 31' is formed to run from the groove 20 to the front end 50. Recesses 48 are formed in the upper valve body to allow for alignment of the upper valve body to the lower valve body and seal in the sample probe 16 within the channel. Alternatively, as shown in FIG. 3A, the upper valve body may be comprised of two individual sections. This embodiment includes a front elastomeric guide section 12' which includes a channel 20, elbow channel 31', wash channel 30' and recesses 48 similar to the arrangement found in FIG. 3. A front section 12" is positioned in front of the front elastomeric guide section 12' and covers the groove and probe during operation. The front section 12 may be made from any solid bearing material that is capable of sealing the probe within the channel.

Figure 4:
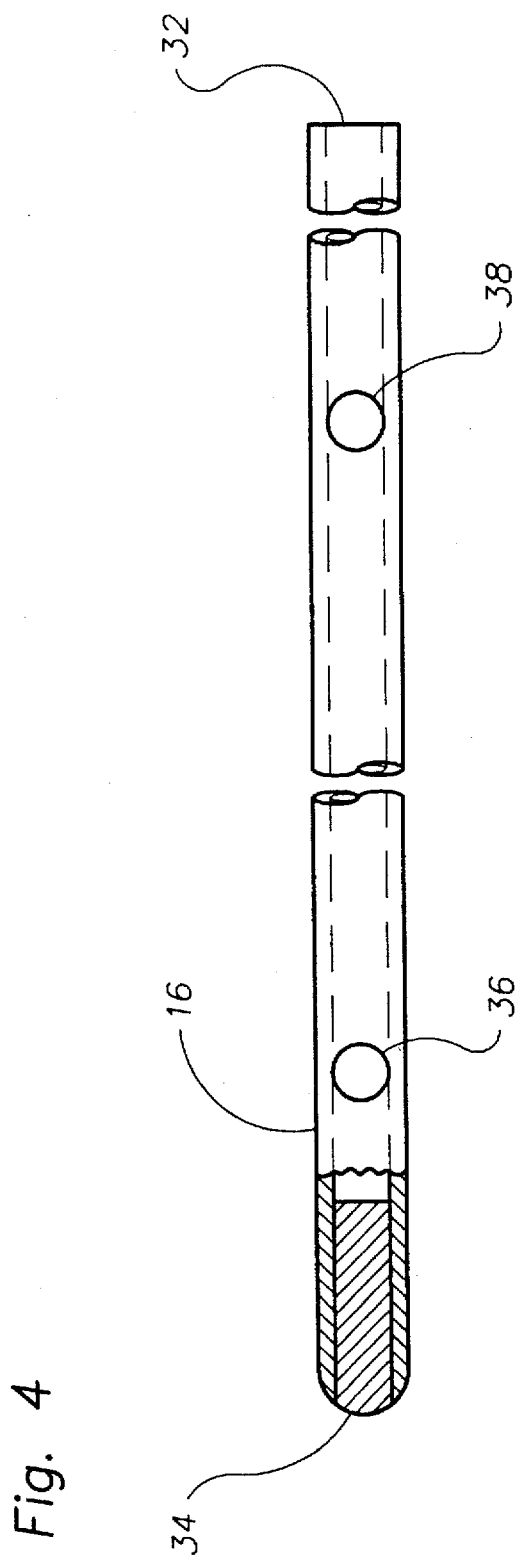
FIG. 4 is a side view of the sample probe of the invention.

FIG. 4 illustrates the sample probe 16 of the invention. In one embodiment, the sample probe 16 is a hollow tube comprising a sealed end 34 and an open end 32. A sample aperture 36 is located adjacent to the sealed end and is formed into the side wall of the sample probe 16. The sample aperture 36 functions to take samples into the sample probe when that portion of the sample probe is positioned in a sample container. The sealed end 34 permits the sample probe to be moved within the assembled valve bodies 12, 14 and allows the sample aperture 36 to be sealed within the valve as the sample probe 16 is withdrawn into the assembled valve bodies.

A reagent aperture 38 is formed into the side wall of the sample probe between the sample aperture 36 and the open end 32. The reagent aperture 38 permits reagents to flow into the sample probe 16 when the reagent aperture is aligned with any one of the reagent inlet ports 22. The distance between the sample aperture 36 and the reagent aperture 38 is such that when the reagent aperture 38 aligns with any one of the inlet ports 22, the sample aperture 36 is sealed, and when the sample aperture 36 is positioned beyond the front end 28 of the valve, the reagent aperture 38 becomes sealed.

The sample probe may be made of any material that does not react with the biological sample or any of the reagents or washing solutions used in the invention. Such materials include surgical stainless steel, teflon, or other nonreactive materials. In one embodiment, the sample probe is made of surgical stainless steel with an inner diameter of approximately 0.002 inch and apertures 36, 38 have a diameter of approximately 0.017 inch. In general, the thickness of the probe tube wall is less than the probe port diameter so that the port does not form a "blind pocket" which could be a source of cross-contamination of successive samples.

As indicated above, the groove 20 formed in the upper valve body 12 aligns with the groove 18 formed in the lower valve body 14 when the two valve bodies are attached together. The resulting channel formed by the two grooves 18 and 20 has the proper dimensions to fit the sample probe 16 and to allow the sample probe 16 to move longitudinally therewithin. In addition, the dimensions of the resulting channel are such that the apertures 36, 38 located in the sample probe 16 are capable of being sealed when they are not aligned with any inlet port.

Figure 5:
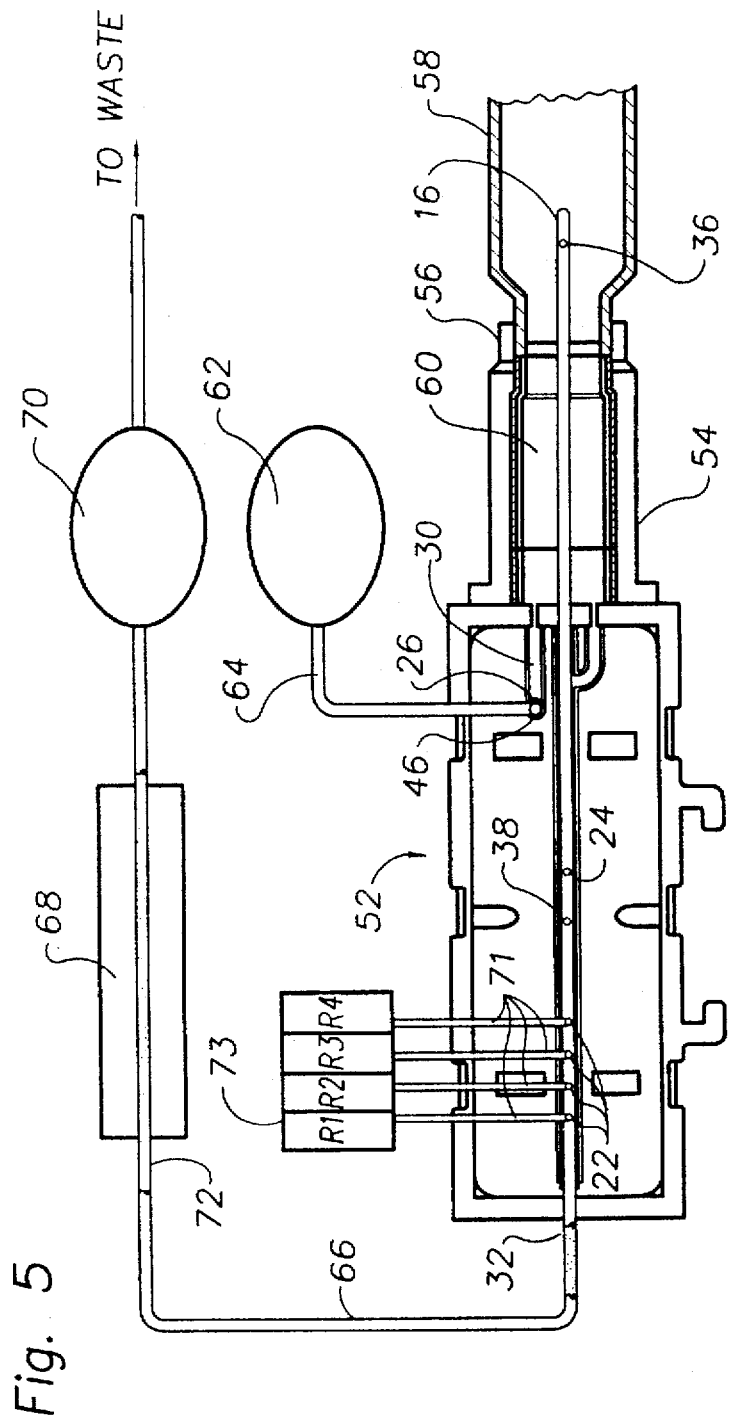
FIG. 5 is a diagram of the multifunction valve of the invention in the "sampling" position.

FIG. 5 illustrates the multifunction valve 52 of the invention connected to devices that enable the multifunction valve to operate in conjunction with other components in an analyzer. In the exemplary embodiment illustrated in FIG. 5, the multifunction valve 52 includes a combination sample input collector and wash chamber 54 attached to the front of the assembled valve bodies. The sample input collector 54 includes a fitting 56 designed to accept a container 58 containing a sample to be analyzed; for example a syringe or capillary containing a sample of blood, urine, or other liquid biological sample. The fitting 56 forms a seal with the container 58 so that no sample is spilled during sample uptake by sample probe 16.

The sample input collector and wash chamber 54 further comprises a chamber 60 in which wash solution or foam is supplied to wash the sample probe 16 between uptake of samples. A wash pump 62 is connected by a supply line 64 to the wash inlet tube 46. A supply of wash solution or foam is pumped through the wash port 26 and channel 30 and into the chamber 60 when the sample probe 16 is in the "wash" position.

The open end 32 of the sample probe is connected by a tube 66 to the analytical section 68 of the instrument. The analytical section includes any device that analyzes biological samples, for example, dissolved gas sensors, ion slective electrodes, or metabolyte sensors.

During sample uptake, a sample pump 70 aspirates a portion of the sample material into the sample probe and tubing and moves it through the device. Waste material is expelled from the sample pump 70 after the analytical measurements are obtained. This arrangement allows a single pump to draw the selected sample through the sensor module without cross-contamination of the sample sources.

The multifunction valve 52 is connected by tubes 71 to reagent bottles 73. Each tube 71 is attached to a respective inlet tube 42 to provide a selected reagent to the multifunction valve. The reagent bottles 73 include reagents (denoted as $R_1$, $R_2$, $R_3$, and $R_4$), such as calibration reagents, quality control reagents, standardization reagents, reaction reagents, or any other solution useful in the analytical device. The reagents contained in the reagent bottles 73 are accessible to the multifunction valve 52 when the reagent aperture 38 is aligned with a selected reagent inlet port 22. Although FIG. 5 is illustrated with four reagent sources ($R_1$–$R_4$), any number of reagent sources may be utilized.

Referring again to FIG. 5, the multifunction valve of the invention is illustrated in the "sampling" position. In this position, a syringe 58 is attached to the fitting 56 to provide a biological sample to be analyzed. The sealed end 34 and the sample aperture 36 are positioned beyond the fitting 56 to enter the syringe 58. In this position, the reagent aperture 38 is not aligned with any of the inlet ports 22. Rather, the reagent aperture 38 in the sample probe is blocked by the wall of the valve body, thus preventing contamination of the blood sample by the other reagent sources. Therefore, the sample 72 is free to move into the analytical section 68 of the instrument without contamination.

Figure 6:
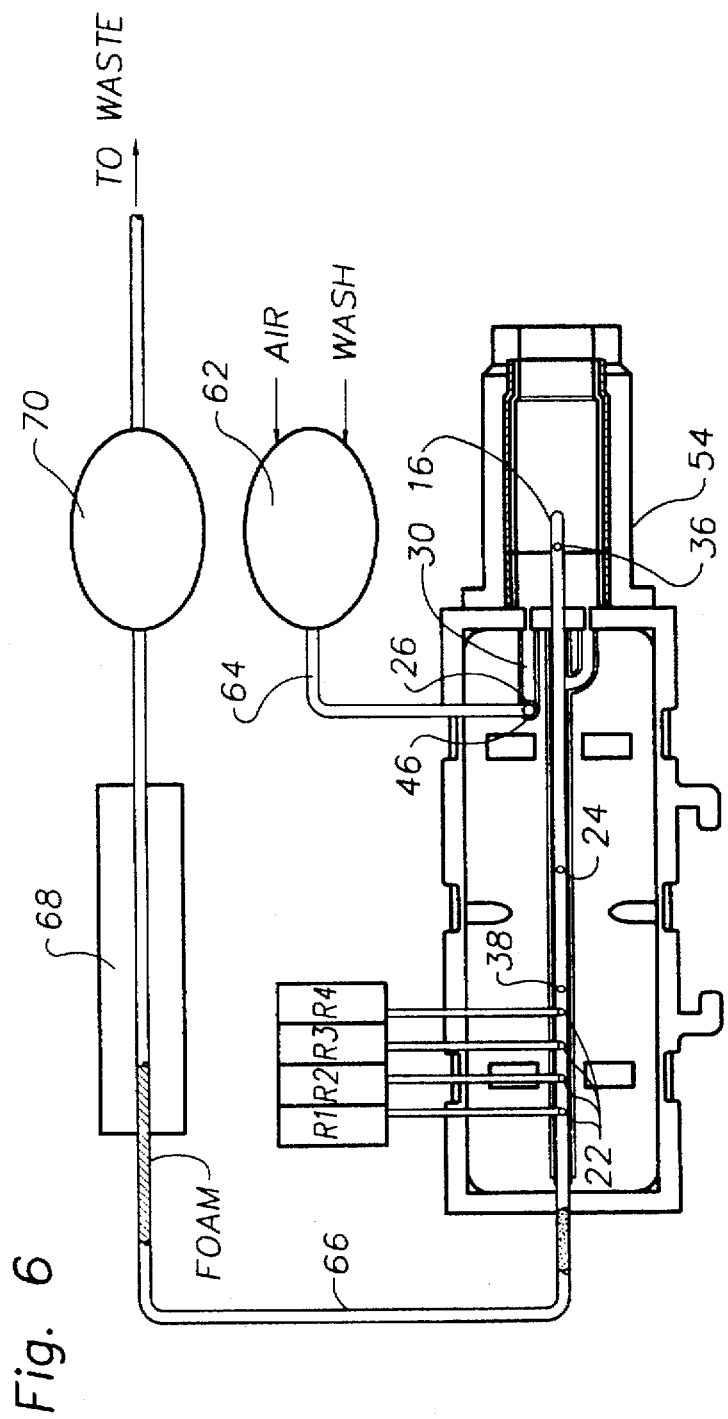
FIG. 6 is a diagram of the multifunction valve of the invention in the "wash" position.

Pump 70 aspirates a sample through sample aperture 36 and into the sample probe. Once a sufficient and known volume of sample is taken into the sample probe and the analytical measurement is made, the valve bodies move to withdraw the tip into the input collector and wash chamber 54. This position is the "wash" position and is illustrated in FIG. 6. Alternatively, the sample probe can be positioned to align the sample aperture 36 with vent aperture 24 to allow an air bubble to be drawn into the sample probe. The bubble is useful as a break between samples of differing composition. As the bubble moves through the flow path, the meniscus at the interface of the sample and the air produce a wiping action which essentially removes the residue of the previous sample.

Referring now to FIG. 6, the sample probe 16 is withdrawn so that the sealed tip 34 and sample aperture 36 are positioned within the input collector and wash chamber 54. In this position, the sample probe tip can be washed with an air/reagent wash foam generated by a pump 62 and delivered through the wash port 26 in the valve body. The foam can be aspirated into the sample probe 16 by the sampling pump 70, thereby washing residual biological material sample from the tip and the inside of the sample probe. As the wash foam is aspirated through the instrument, it washes the tube 66 as well as the analytical section of the sensor 68. In the wash position, the reagent aperture 38 is sealed by the valve bodies in this position so that the reagents are not contaminated by the wash foam.

Figure 7:
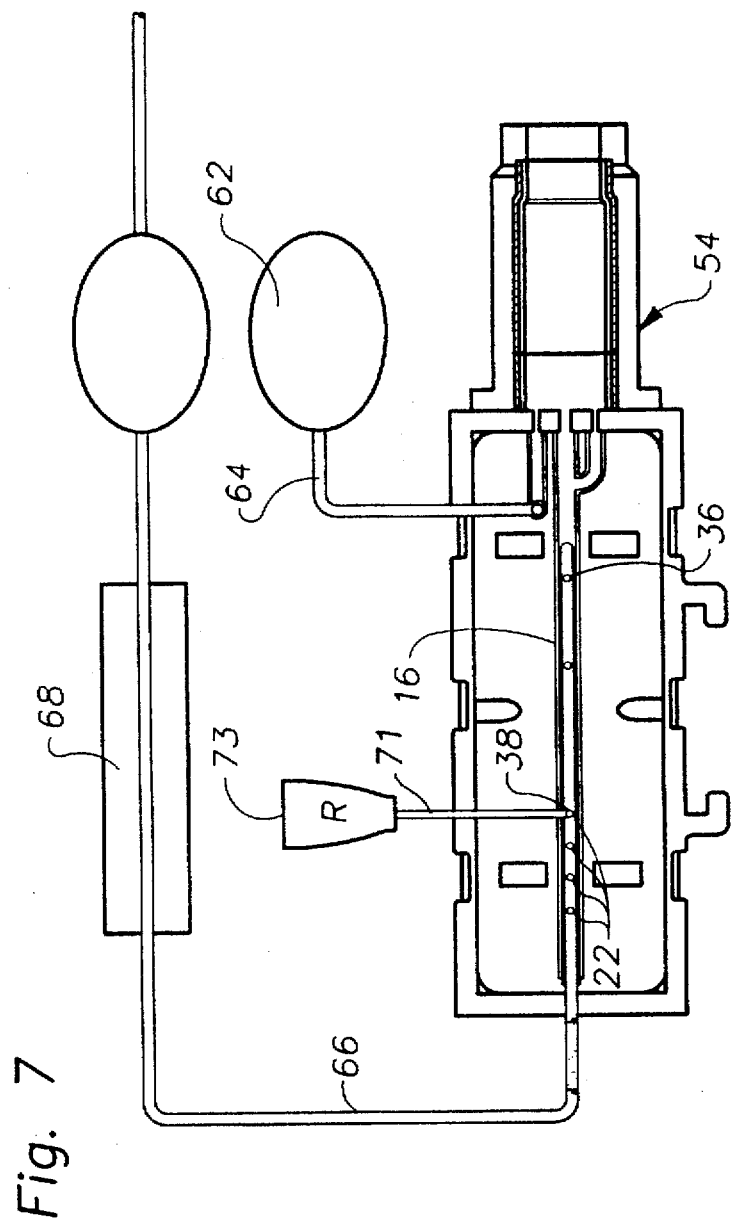
FIG. 7 is a diagram of the multifunction valve of the invention in the "reagent uptake" position.

Referring now to FIG. 7, the multifunction valve is illustrated in the "reagent uptake" position. In this position, the sample probe 16 is retracted into the valve, and the reagent aperture 38 is positioned to align with a selected one of the reagent inlet ports 22. Each reagent inlet port is connected to a reagent container containing a specified reagent, such as a quality control reagent, calibration reagent, standardization reagent, or reaction reagent. Some exemplary reagents include, but are not limited to, pH buffer solutions, glucose solutions, or a standard protein solution. FIG. 7 is illustrated with a single reagent container attached to the multifunction valve for clarity. However, it will be appreciated that any number of reagent containers can be selected by adding reagent inlet ports to the valve, as long as the valve body between the first reagent inlet port and the input/wash area 54 is long enough to block the reagent aperture 38 in the sampling position, and to block the sample aperture 36 in the reagent uptake position. In the reagent uptake position, the sample aperture 36 is sealed by the valve bodies to prevent reagents from entering the input collector and wash chamber 54 and contaminating the samples.

During reagent uptake, the sampling pump 70 aspirates a volume of reagent into the sample probe through the reagent aperture 38. The reagent travels along tube 66 to the analytical section 68 where calibration and/or quality control measurements are made. Following this procedure, the reagent is expelled to waste.

Referring now to FIG. 8, the multifunction valve of the invention is illustrated in three positions and connected to a motive apparatus 80 and a control module 82. FIG. 8 includes the multifunction valve of the invention 52, a motor 80, such as a stepper motor or other motor, and a control module 82, such as a computer. The control module 82 is capable of instructing the motor to move the valve body relative to the sample probe according to the operational cycle desired by the operator. The control module 82 is also capable of controlling the pumps 70, 62 to aspirate reagents or uptake samples.

FIG. 8A shows a diagram of the invention in the "sampling" position. The motor is connected to the multifunction valve body by control arms 84 which position the valve so that the sealed tip 34 of the sample probe is exposed and ready to accept a sample. The control module 82 can also instruct the sampling pump 70 to take in a sample. In FIG. 8B, the control module instructs the motor to move the valve body so that the sealed tip 34 is located in the wash chamber 54. At this point, the control module will activate the pumps 62, 70. The wash pump 62 is instructed to dispense wash foam or solution into the wash chamber, and the sampling pump is instructed to take up the wash solution to clean the interior of the sample probe. In FIG. 8C, control module again instructs the motor 80 to move the valve body so that the sealed tip 34 is located in valve body. At this point, the reagent aperture is aligned with a reagent inlet port, and the sample pump is instructed to take up a volume of reagent. Thus, the valve body is moved as the sample probe is retained in a stationary position. Alternatively, it is possible to retain the valve body in a stationary position and move the sample probe using the motor 80, control arms 84 and control module 82. Thus, the desired valve position may be easily selected by the user to perform the desired operation.

Although the invention has been shown and described with respect to an illustrative embodiment thereof, it should be appreciated that the foregoing and various other changes, omissions, and additions in the form and detail thereof may be made without departing from the spirit and scope of the invention as delineated in the claims.

We claim:
1. A multifunction valve, comprising:
   a lower valve body, comprising
      a first end, a second end, a top face, and a bottom face;
   an upper valve body, comprising
      a first end, a second end, a top face, and a bottom face, said upper valve body attached to said lower valve body to form a seal; and a groove positioned on said top face and between said first end and said second end of at least one of said valve bodies;

a plurality of inlet ports positioned on at least one of said bottom faces, said plurality of inlet ports having corresponding apertures communicating with said groove;

a sample probe movably positionable in said groove, and comprising a sealed end and an open end adapted to receive a conduit of a fluid test system; and a first aperture located adjacent said sealed end, and a second aperture located between said first aperture and said open end;

said seal sealing said sample probe in said groove;

wherein when said second aperture of said sample probe aligns with one of said plurality of inlet ports to expose an inlet port to said open end, said first aperture of said sample probe is sealed by upper valve body and said lower valve body, and when said first aperture of said sample probe is positioned beyond said first end of said lower valve body said second aperture of said sample probe is sealed by said upper valve body and said lower valve body.

2. The multifunction valve of claim 1, further comprising a sample input collector attached to said first end of at least one of said valve bodies, said sample input collector having a chamber to receive said sample probe and having a holder to receive a container containing a sample to be analyzed.

3. The multifunction valve of claim 2, further comprising a wash port and flow slot, said wash port and said flow slot formed on said top face of at least one of said valve bodies and connected to said chamber of said input collector.

4. The multifunction valve of claim 1, wherein at least one of said plurality of inlet ports is connected to a calibration reagent.

5. The multifunction valve of claim 1, wherein at least one of said plurality of inlet ports is connected to a quality control reagent.

6. The multifunction valve of claim 1, wherein at least one of said plurality of inlet ports is open to the atmosphere.

7. The multifunction valve of claim 1, further comprising a pump and a sensor module attached to said open end of said sample probe.

8. The multifunction valve of claim 2, wherein said multifunction valve has a sample uptake position wherein said first aperture of said sample probe is positioned beyond said sample input collector, and said second aperture is sealed by said upper valve body and said lower valve body.

9. The multifunction valve of claim 2, wherein said multifunction valve has a wash position wherein said first aperture of said sample probe is positioned within said chamber of said sample input collector, and said second aperture is sealed by said upper valve body and said lower valve body.

10. The multifunction valve of claim 2, wherein said multifunction valve has a calibration position wherein said second aperture of said sample probe aligns with one of said plurality of inlet ports and said first aperture of said sample probe is sealed by said upper valve body and said lower valve body.

11. An instrument to analyze samples of biological material, comprising:

the multifunction valve of claim 1;

a sample input collector attached to said first end of at least one of said valve bodies of said multifunction valve, said sample input collector having a chamber to receive said sample probe and having a holder to receive a container containing a sample to be analyzed;

a first pump and a sensor module attached to said open end of said sample probe;

a second pump connected to a wash port;

at least one reagent container, each of said at least one reagent container connected to a corresponding one of each of said plurality of inlet ports; and motion and control apparatus to move said multifunction valve.

12. The instrument of claim 11, wherein said multifunction valve has a sample uptake position wherein said first aperture of said sample probe is positioned beyond said sample input collector, and said second aperture is sealed by said upper valve body and said lower valve body.

13. The instrument of claim 11, wherein said multifunction valve has a wash position wherein said first aperture of said sample probe is positioned within said chamber of said sample input collector, and said second aperture is sealed by said upper valve body and said lower valve body.

14. The instrument of claim 11, wherein said multifunction valve has a calibration position wherein said second aperture of said sample probe aligns with one of said plurality of inlet ports and said first aperture of said sample probe is sealed by said upper valve body and said lower valve body.

15. The instrument of claim 11, wherein said instrument analyzes biological material.

16. The instrument of claim 15, wherein said biological material is blood.

17. The instrument of claim 15, wherein said biological material is urine.

* * * * *